(12) United States Patent
Wojtkowski

(10) Patent No.: US 6,809,206 B2
(45) Date of Patent: Oct. 26, 2004

(54) METHOD FOR ACYLATING CYCLIC COMPOUNDS

(75) Inventor: Paul Walter Wojtkowski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 46 days.

(21) Appl. No.: 10/396,047

(22) Filed: Mar. 24, 2003

(65) Prior Publication Data

US 2003/0232984 A1 Dec. 18, 2003

Related U.S. Application Data

(63) Continuation-in-part of application No. 09/833,451, filed on Apr. 12, 2001, now abandoned, which is a continuation-in-part of application No. 09/483,644, filed on Jan. 14, 2000, now abandoned.
(60) Provisional application No. 60/120,213, filed on Feb. 12, 1999.

(51) Int. Cl.[7] .................. C07D 231/04; C07D 335/06; C07C 321/04
(52) U.S. Cl. .................. 548/364.4; 549/23; 568/23
(58) Field of Search .................. 548/364.4; 549/23; 568/23

(56) References Cited

U.S. PATENT DOCUMENTS

| | | |
|---|---|---|
| 2,672,483 A | 3/1954 | Thomas |
| 4,560,403 A | 12/1985 | Motojima et al. |
| 4,678,496 A | 7/1987 | Motojima et al. |
| 4,695,673 A | 9/1987 | Heather et al. |
| 5,480,858 A | 1/1996 | Sakamoto et al. |
| 5,523,462 A | 6/1996 | Kast et al. |
| 5,559,218 A | 9/1996 | Kast et al. |

FOREIGN PATENT DOCUMENTS

| | | |
|---|---|---|
| EP | 0283261 | 9/1998 |
| EP | 0666254 | 4/1999 |
| WO | WO 9308153 | 4/1993 |
| WO | WO 9622957 | 8/1996 |
| WO | WO 9622958 | 8/1996 |
| WO | WO 9701550 | 1/1997 |
| WO | WO 9928282 | 6/1999 |

OTHER PUBLICATIONS

Chemical Reviews 1999, 99(4), p. 1047–1065, D. B. Rubinov et al. "Chemistry of 2–Acylcycloalkane–1,3–diones".

Sheny–Yien Liu, Yukio Ogihara, Yakugaku Zasshi 1975, 95(9), 1114–1118.

Ali A. Alfatafta et al., J. Nat. Prod. 1994, 57(12), 1696–1702.

Synthesis 1978, pp. 925–926.

M. Fuji, Natural Medicines (1996), V50,P404.

*Primary Examiner*—Taofiq Solola

(57) ABSTRACT

The method of this invention prepares acylated cyclic compounds by contacting phenyl esters as acylating agents with cyclic compounds in the presence of a cyanide or fluoride catalyst.

15 Claims, No Drawings

METHOD FOR ACYLATING CYCLIC COMPOUNDS

BACKGROUND OF THE INVENTION

Acylated cyclic 1,3-dicarbonyl compounds and salt derivatives represented by the triketone tautomer of Formula i:

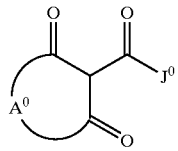

wherein linking group $A^0$ completes a 5-, 6- or 7-membered, optionally substituted carbocyclic or heterocyclic ring, and $J^0$ is an aliphatic or aromatic group, are well known in the literature. Examples of such compounds are disclosed in European Patent Application Publication EP-666254-A1, PCT Patent Application Publications WO96/22958 and WO97/01550, and U.S. Pat. Nos. 2,672,483, 4,560,403, 4,678,496 and 5,480,858.

Cyclic 1,3-dicarbonyl compounds of Formula i are known to equilibrate with enolic tautomer forms, such as Formula ia:

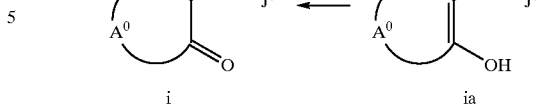

As equilibration between the triketone of Formula i and its enolic tautomers is facile, they are chemical and biological equivalents. Through this equilibration the 1,3-dione moiety is equivalent to its enolic 3-hydroxy-2-en-1-one tautomers. These compounds are acidic and easily form salts on treatment with bases. As the free acid and salt forms of these compounds rapidly equilibrate in the environment and under physiological conditions, they can be considered biological equivalents.

Many of the acylated 1,3-dicarbonyl compounds of Formula i are known to be biologically active. Examples of such compounds are disclosed in PCT Patent Application Publication WO97/01550 as valuable for controlling undesired vegetation in such important crops as rice, soybeans, sugar beets, corn (maize), potato, wheat, barley, tomato and plantation crops. U.S. Pat. Nos. 4,560,403 and 4,678,496 indicate compounds in this class are also plant growth regulants, both for crop and non-crop uses such as for lawns. In *Chemical Reviews* 1999, 99(4), pages 1047–1065, D. B. Rubinov et al. published "Chemistry of 2-Acylcycloalkane-1,3-diones" in which he reviews the chemistry of this class of compounds as well as their usefulness. Rubinov indicates that these compounds exhibit antibiotic, antibacterial, antihelmintic, antimalarial, antidiabetic, anticancer and other useful therapeutic properties. Plants and fruits used as folk medicines may be extracted to yield flavanoids with this basic structure.

Examples of specific compounds represented by Formula i with commercial significance are shown in Table 1.

TABLE 1

Commercially Useful Triketones

| STRUCTURE | IDENTITY | USE |
|---|---|---|
| | Sulcotrione<br>CAS 99105-77-8 | Pre and post emergence control in maize of annual and broadleaf grasses. |
| | 2-isovalerylindane-1,3-dione<br>CAS 83-28-3 | Insecticide.<br>Rodenticide. |
| | Pindone<br>CAS 83-26-1 | Anticoagulant,<br>Rodenticide |

TABLE 1-continued

Commercially Useful Triketones

| STRUCTURE | IDENTITY | USE |
|---|---|---|
| | Chlorophacinone CAS 3691-35-8 | Anticoagulent, Rodenticide |
| | Difenadione CAS 82-66-6 | Anticoagulant Rodenticide |
| | Dehydroacetic acid CAS 520-45-6 | Sodium salt as dip-fungicide, Bacteriacide in toothpastes. Plasticizer. |
| | Pyratrione CAS 51089-21-5 | Anti-hypertensive. |
| | Prohexadione CAS 88805-35-0 | Plant growth regulator. |
| | 2,5-dihydroxy-3-methoxy-6-[(2E)-1-oxo-3-phenyl-2-propenyl]-2,5-cyclohexadiene-1,4-dione | Extract from *Didymocarpus leucocalyx* (M. Fujii, Natural Medicines 1996, V50, p404) |
| | 4,5-dimethoxy-2-[(2E)-1-oxo-3-phenyl-2-propenyl]-4-cyclopentene-1,3-dione | Flavanoids from the fruits of *Lindera erythrocarpa*, used as a folk medicine. (Sheng-Yien Liu, Yukio Ogihara, Yakugaku Zasshi 1975, 95(9), 1114–18) |

TABLE 1-continued

Commercially Useful Triketones

| STRUCTURE | IDENTITY | USE |
|---|---|---|
| (structure of Apiosporamide) | Apiosporamide | Antifungal extract from mycelium of the coprophilous fungus. (Ali A. Alfatafta et al. J. Nat. Prod. 1994, 57(12), 1696–702) |
| (structure of Compound 79) | Compound 79 Table II Page 36 of EP 0 283 261 B1 | EP 0 283 261 B1 "Herbicidal Substituted Cyclic Diones" |
| (structure of Compound 74) | Compound 74 Table I Page 34 of EP 0 283 261 B1 | EP 0 283 261 B1 "Herbicidal Substituted Cyclic Diones" |

Scheme i shows preparation of acylated cyclic 1,3-dicarbonyl compounds of Formula i, via rearrangement of the corresponding enol ethers of Formula ii, wherein linking group $A^0$ and $J^0$ are as already described. Such a rearrangement is disclosed in a number of references including PCT Patent Application Publications WO99/28282 and WO96/22958, and U.S. Pat. Nos. 4,695,673 and 4,678,496.

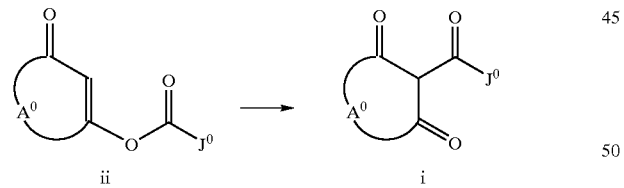

Scheme i

The reaction requires a catalyst to proceed in satisfactory rate and yield. Known catalysts include azoles such as 1,2,4-triazole as described in PCT Patent Application Publication WO99/28282, 4-(dimethylamino)pyridine as described in PCT Patent Application Publication WO93/08153, cyanide as described in U.S. Pat. No. 4,695,673 and aluminum trichloride as described in *Synthesis* 1978, pages 925–6.

As described in PCT Patent Application Publication WO99/28282 and shown in Scheme ii, some enol ethers of Formula ii can be prepared by treating a 1,3-dicarbonyl compound of Formula iii with an acylating reagent of Formula iv in the presence of a base.

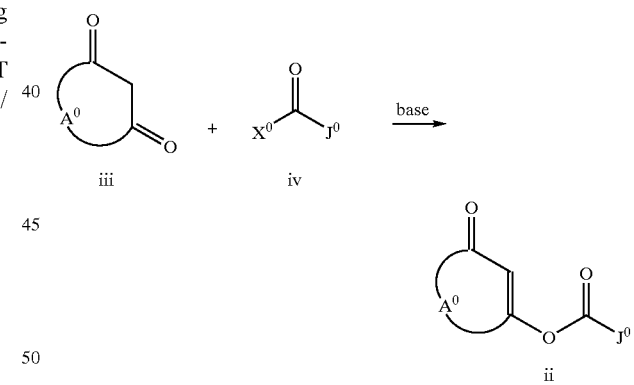

Scheme ii wherein linking group $A^0$ completes a 5-, 6- or 7-membered optionally substituted carbocyclic or heterocyclic ring. $J^0$ is an aliphatic or aromatic group, and $X^0$ is a halogen leaving group, usually chlorine.

PCT Patent Application Publications WO99/28282, WO96/22958 and WO96/22957, and U.S. Pat. Nos. 5,559,218, and 5,480,858 describe acyl halides as suitable acylating agents. The enol ether may be isolated, or the crude reaction mass may be treated with a catalyst, as indicated above to give the desired acylated cyclic 1,3-dicarbonyl compounds of general Formula i. A limitation of the method of Scheme ii is that acyl halides are produced under acidic conditions that can decompose acid-sensitive chemical substituents on the acyl halide itself causing reduced yield and purity. Also, substituents that would react with the highly reactive acyl halide group cannot be included. Additional methods to prepare acylated cyclic 1,3-dicarbonyl compounds are therefore needed.

SUMMARY OF THE INVENTION

This invention pertains to a method for preparing an acylated product of Formula 1:

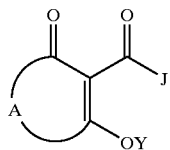

wherein

A is a linking group comprising an optionally substituted backbone segment consisting of 2 to 4 atoms selected from carbon atoms and 0 to 2 nitrogen, 0 to 2 oxygen and 0 to 2 sulfur atoms;

J is an optionally substituted, carbon-linked hydrocarbyl group; and

Y is H or a salt cation;

the process comprising contacting a phenyl ester of Formula 2:

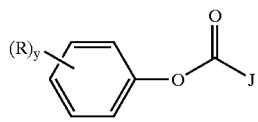

wherein y is 0, 1, 2 or 3;

each R is independently selected from electron-withdrawing groups; and

J is as defined for Formula 1 with a cyclic compound of Formula 3:

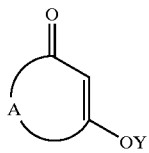

wherein

A and Y are as defined for Formula 1;

in the presence of a source of cyanide or fluoride ion.

DETAILS OF THE INVENTION

The following definitions apply throughout the disclosure and claims of this invention. The term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butyl pentylsulfonyl and hexylsulfonyl isomers. "Alkenylthio", "alkenylsulfinyl", "alkenyl-sulfonyl", "alkynylthio", "alkynylsulfinyl", "alkynylsulfonyl", and the like, are defined analogously to the above examples. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkenyl" includes groups such as cyclopentenyl and cyclohexenyl as well as groups with more than one double bond such as 1,3- and 1,4-cyclohexadienyl. By "carbocycle" is meant a ring having a backbone consisting only of carbon atoms. By "heterocycle" is meant a ring having a backbone in which at least one atom is other than carbon. Unless indicated otherwise, heterocyclic ring systems can be attached through any available carbon or nitrogen by replacement of a hydrogen on said carbon or nitrogen. The term "aryl" means a radical derived from an aromatic ring system. By "aromatic" is meant fully unsaturated carbocycles and heterocycles where the Hückel rule is satisfied for an aromatic ring. In aromatic rings each of the ring atoms is essentially in the same plane and has a p-orbital perpendicular to the ring plane, and in which (4n+2) π electrons, where n is 0 or a positive integer, are associated with the ring to comply with Huckel's Rule. The term "halogen", either alone or in compound words such as "haloalkyl", includes fluorine, chlorine, bromine or iodine. When used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive. When a group is stated to be optionally substituted, the substituents are independently selected, and unless a number is indicated, the number of substituents may vary between 0 and the number of hydrogen atoms available for replacement by substituents.

As shown in Scheme 1, the process of the invention involves reaction of cyclic compound of Formula 3 with a phenyl ester of Formula 2 to give the acylated cyclic compound of Formula 1 and a phenol derivative of Formula 4 byproduct.

Scheme 1

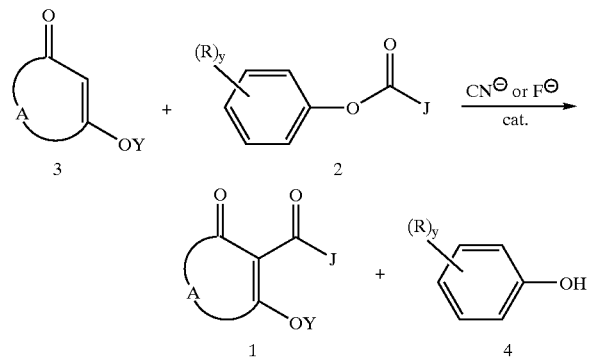

wherein A, J, Y, R and y are as defined in the Summary of the Invention.

In the process of Scheme 1, the phenyl ester of Formula 2 serves as the acylating agent. Phenyl esters of Formula 2 have been discovered to give good to excellent yields of the acylated products of Formula 1 in the presence of cyanide or fluoride ion even though they are inherently less reactive acylating agents than the acyl chlorides used in processes previously known in the art. Not only are the phenyl esters of Formula 2 found to work well to provide the acylated products of Formula 1 from the cyclic compounds of Formula 3 in a single process step, but they can be prepared under mild, acid-free conditions preserving sensitive functionality vulnerable to degradation under reaction conditions used to prepare the acyl chlorides of the prior art processes. As the process of Scheme 1 also involves mild reaction conditions, it provides a very general method useful for preparing acylated products of Formula 1 of very broad scope of chemical structure and functionality.

The process as shown in Scheme 1 requires at least a catalytic amount of cyanide or fluoride ion. Suitable cyanide sources include, but are not limited to, inorganic salts such as zinc cyanide and alkali metal salts including sodium cyanide and potassium cyanide, and organic compounds such as hydrogen cyanide and acetone cyanohydrin. The amount of cyanide source is typically greater than 0.01 equivalents relative to the compound of Formula 3, preferably between 0.05 and 0.3 equivalents.

Suitable fluoride sources include, but are not limited to, ammonium, phosphonium and inorganic fluoride salts, particularly alkali metal fluoride salts such as lithium fluoride, sodium fluoride, potassium fluoride, rubidium fluoride, cesium fluoride, ammonium fluoride, ammonium silicofluoride, tetramethylammonium fluoride, tetrabutylammonium fluoride and tetrabutylphosphonium fluoride.

Hydrogen fluoride can also be used with an equivalent of a base to convert it to a salt. Preferred sources include cesium fluoride and potassium fluoride, especially spray-dried potassium fluoride. The amount of fluoride ion is typically greater than 0.5 equivalents versus the compound of Formula 3, preferably, between 0.5 and 5.0 equivalents. The usefulness of fluoride in the process of the present invention is especially surprising, as fluoride has not been reported useful in the method of the prior art (shown in Scheme a).

To achieve rapid reaction and good yields, the method of Scheme 1 advantageously includes a source of basicity. If the starting cyclic compound of Formula 3 is present as the salt (i.e. Y is a salt cation), then the Formula 3 salt itself is generally a sufficient source of basicity, and the Formula 1 product will be produced also as the salt with the same salt cation. If the starting cyclic compound of Formula 3 is present as the free acid form (i.e. Y is H), then an added source of basicity is generally needed to achieve rapid reaction and good yields. At least about a full equivalent, and preferably more than two equivalents, of a fluoride or cyanide salt can provide not only catalysis but also the required source of basicity. Fluoride salts work particularly well as both catalyst and a source of basicity to give good conversion rates and yields when at least 3 equivalents of fluoride salt is present in the reaction mixture relative to the starting material of Formula 3. If the phenolic byproduct of Formula 4 is acidic enough to protonate fluoride, at least 4 equivalents of fluoride salt may be needed to obtain best results. When a fluoride salt is used as the source of basicity, the reaction product of Formula 1 may still be isolated in the free acid form (i.e. Y is H) on adding water to the reaction mixtures, possibly because in aqueous solution hydrofluoric acid appears to have greater acidity than most acylated cyclic compounds of Formula 1. If a catalytic amount of fluoride or cyanide salt is used, then generally at least one equivalent of an additional base is needed to provide a source of basicity, and the product of Formula 1 is formed as the salt of that base (i.e. Y in Formula 1 is a salt cation).

Suitable bases that can be used in the invention include organic compounds such as organic amines, including tertiary amines, optionally substituted heterocycles such as pyridine, and the like, whose conjugate acids have a $pK_a$ of greater than 4. "Tertiary amines" are derivatives of ammonia that are substituted with three independently selected carbon-connected groups, whose connecting carbon atoms are not bonded to heteroatoms such as oxygen, nitrogen or sulfur. Typical tertiary amine substituents are alkyl and aryl, although other groups such as haloalkyl, alkenyl and alkynyl are possible. Tertiary amines include alkylamines such as trimethylamine, triethylamine, tributylamine, diisopropylethylamine, and the like, and alkylaminobenzenes such as N,N-dimethylaminobenzene, N,N-diethylaminobenzene, and the like. Suitable bases also include ionic bases such as, but not limited to, alkali metal carbonates such as lithium carbonate, sodium carbonate, potassium carbonate, rubidium carbonate and cesium carbonate, alkali metal and alkaline earth metal oxides such as lithium oxide, sodium oxide, calcium oxide, strontium oxide and barium oxide, alkali metal and alkaline earth metal hydrides such as calcium hydride, sodium hydride and potassium hydride, alkali metal and alkaline earth metal hydroxides such as lithium hydroxide, calcium hydroxide, barium hydroxide, sodium hydroxide, potassium hydroxide, rubidium hydroxide, cesium hydroxide and tetraalkylammonium hydroxides, alkoxides such as sodium ethoxide and potassium tert-butoxide, and the like. For reason of solubility, preferred ionic bases are those containing an alkali metal or tetra($C_1$–$C_4$)alkylammonium cation. Lithium carbonate, sodium carbonate and potassium carbonate are particularly useful as bases. The amount of base used is generally 1 equivalent or greater with respect to the compound of Formula 3, with 1–3 equivalents being preferred. If the compound of Formula 3 in the salt form (i.e. Y is a salt cation) is used in place of the compound of Formula 3 wherein Y is H, then the base can be omitted.

One skilled in the art recognizes that when the base is lithium carbonate (or hydroxide), sodium carbonate (or hydroxide), potassium carbonate (or hydroxide), calcium hydroxide or tetra-n-butylammonium hydroxide, then Y will be $Li^+$, $Na^+$, $K^+$, $Ca^{2+}$ or tetra-n-butylammonium, respectively. When the base is an alkylamine, then Y will be the corresponding alkylammonium salt. For example, when trimethylamine is the base, then Y will be trimethylammonium. Because Y is provided by the base, the base used in the reaction is described as a basic source of Y. Y then is typically selected from alkali metal cations such as $Li^+$, $Na^+$ and $K^+$, alkaline earth metal cations such as $Ca^{2+}$, $Sr^{2+}$ and $Ba^{2+}$, tri($C_1$–$C_4$ alkyl)ammonium, tetra($C_1$–$C_4$ alkyl)ammonium, and protonated N,N-di($C_1$–$C_4$ alkyl)aminobenzene. To obtain best solubility, Y is preferably selected from alkali metal cations such as $Li^+$, $Na^+$ and $K^+$, tri($C_1$–$C_4$ alkyl)ammonium, tetra($C_1$–$C_4$ alkyl)ammonium, and protonated N,N-di($C_1$–$C_4$ alkyl)aminobenzene. For reason of cost, Y is most preferably selected from $Na^+$, $K^+$, tri($C_1$–$C_4$ alkyl)ammonium, and protonated N,N-di($C_1$–$C_2$ alkyl)-aminobenzene.

A phase transfer catalyst is optionally added. This is especially advantageous if a non-polar solvent is used and the cyanide or fluoride source is an inorganic salt. Examples of phase transfer catalysts that can be used are tetraalkylammonium salts, such as tetrabutylammonium chloride, cetyltrimethylammonium bromide and the like, organic phosphonium salts such as tetrabutylphosphonium chloride, tetraphenylphosphonium bromide and the like, and both cyclic and acyclic polyethers such as the various crown ethers, diglyme, triglyme, higher molecular weight polyethylene glycol ethers and the like. The amount of phase transfer catalyst is typically greater than 0.1 equivalents relative to the cyanide or fluoride source. Preferably 0.1 to 1.0 equivalents are used. Phase transfer catalysis is particularly advantageous when an alkali metal cyanide source is used. In this case the cyanide anion may not have sufficient solubility in the reaction solvent to produce a practical rate of reaction. A "phase transfer catalyst" possesses the quality of increasing the solubility of the cyanide or fluoride anion in the reaction phase and in effect transferring it from the phase it is more soluble in to that in which it is required for promoting the desired reaction.

The process is generally carried out in a suitable solvent. By "suitable solvent" is meant a liquid wherein the compounds of Formula 2 can be dissolved or suspended and the process proceeds at a commercially acceptable rate. Any aprotic solvent can be employed, providing that it is inert in the reaction of the present invention and that the reagents have adequate solubility. Examples of aprotic solvents include nitriles such as acetonitrile, propionitrile and adiponitrile, ethers such as tetrahydrofuran and dioxane, ketones such as acetone and methyl ethyl ketone, aromatics such as benzene, methylbenzene, dimethylbenzenes and chlorobenzene, esters such as ethyl acetate, amides such as N,N-dimethylformamide, N,N-dimethylacetamide and N-methylpyrrolidone, sulfoxides such as dimethyl sulfoxide (alternatively named methyl sulfoxide) and tetramethylene sulfoxide, and sulfones such as dimethyl sulfone (alternatively named methyl sulfone) and sulfolane (alternatively named tetramethylene sulfone). Preferred are the nitrile and sulfoxide solvents.

The reaction temperature may be chosen to obtain a commercially practical reaction rate without adversely affecting reaction yield through production of unwanted byproducts. Typically, the reaction temperature is maintained between 0° C. and 250° C., for from 0.5 to 130 hours for complete conversion. The preferred temperature range is from 40° C. to 100° C., wherein most reactions are complete within 2 to 4 hours.

The reaction may be conducted at any pressure compatible with the chosen solvent and reaction temperature. The preferred pressure is from 1 to 3 atmospheres ($1\times10^5$ to $3\times10^5$ Pa). For sake of convenience and simplicity, operation at about 1 atmosphere ($1\times10^5$ Pa) is most preferred.

The reaction is performed by combining the ingredients, then maintaining a suitable temperature and pressure for a period of time until the desired conversion of the compound of Formula 3 to the compound of Formula 1 has occurred. The product can be isolated by standard methods, e.g., by filtration. The product is isolated as the free acylated cyclic compound of Formula 1 (Y is H) or as its salt (Y is a salt cation). The salt of Formula 1 (Y is a salt cation) can be converted to the free acid-form of the acylated cyclic product of Formula 1 (Y is H) by treatment with acid having a $pK_a$ lower than the $pK_a$ of the product of Formula 1 wherein Y is H. At least one equivalent of acid is needed per mole of salt of Formula 1 (Y is a salt cation). Preferred are acids having a $pK_a$ less than about 3. More preferred as acids having a $pK_a$ less than about 2. Most preferred are strong mineral acids such as hydrochloric acid, sulfuric acid and phosphoric acid. Conversely, the free acylated cyclic compound of Formula 1 (Y is H) can be converted to its salt (Y is a salt cation) by treatment with a base providing the desired counter ion as the cation.

In the process of Scheme 1, the phenyl esters of Formula 2 are substituted with 0 to 3 substituents R, wherein each R is independently selected from electron-withdrawing groups. By "electron withdrawing group" is meant a functional group attached to the phenyl group of Formula 2 which attracts electrons to itself to a greater extent than would a hydrogen atom in the same position. The attraction of electrons can occur through an "inductive" and or "resonance" effect. Additional information regarding these effects can be found on pages 17–19 and page 36 of *Advanced Organic Chemistry*, 4th Edition by J. March; John Wiley & Sons; New York (1992). Electron-withdrawing groups can accelerate the rate of the reaction for the process of Scheme 1. Particularly useful electron-withdrawing groups for R include $NO_2$, $COOR^1$, $COR^1$, $SO_2R^1$, CN, $CF_3$, F, CON$(R^1)_2$ and $SO_2N(R^1)_2$ wherein each $R^1$ is independently selected from $C_1$–$C_6$ alkyl groups. Most preferred in the reaction of the invention are esters of Formula 2 wherein R is located in the ortho or para position with respect to the phenolic oxygen.

The J group in Formula 2 is an appendage not directly involved in the acylation reaction center. Because the reaction conditions of the process of Scheme 1 as well as those of processes useful for preparing compounds of Formula 2 are so mild, J can accommodate a wide range of molecular structural features and all but the more reactive functionalities known to those skilled in the art. Thus J is best generally described as an optionally substituted hydrocarbyl group bound through a carbon atom to the carbonyl moiety of Formula 2. J is connected through carbon to the carbonyl moiety to provide phenyl esters of Formula 2, which have the appropriate stereoelectronic profile and reactivity for the process of Scheme 1. By "hydrocarbyl" group is meant a radical comprising at least one carbon and at least one hydrogen atom, and optionally containing heteroatoms. For sake of illustration, the carbon atom of J linking to the carbonyl moiety of Formula 2 can be part of an alkyl, alkenyl, alkynyl, cycloalkyl, cycloalkenyl or aryl group, which are optionally substituted with independently selected substituents. Illustrative aryl groups include benzene (phenyl), thiophene, pyridine, pyridazine, pyrazine, pyrimidine, pyrrole, triazine, triazole, furan and related structures. Illustrative substituents include alkyl, alkenyl, alkynyl, cycloalkyl, cycloalkenyl, cycloalkyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, aryloxy, alkylthio, alkenylthio, alkynylthio, alkylsulfinyl, alkenylsulfinyl, alkynylsulfinyl, arylsulfinyl, alkylsulfonyl, alkenylsulfonyl, alkynylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyloxy, alkenylaminocarbonyloxy, alkynylaminocarbonyloxy, arylaminocarbonyloxy, alkoxycarbonylamino, alkenyloxycarbonylamino, alkynyloxycarbonylamino and aryloxycarbonylamino, each further optionally substituted, and halogen, cyano and nitro. The optional further substituents are independently selected from groups like those illustrated above to give groups such as haloalkyl, haloalkenyl and haloalkoxy. The substituents may also be tied together by figuratively removing one to two hydrogen atoms from each of two substituents or a substituent and the supporting backbone and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH$_2$—O—. Tying together a hydroxy group and backbone to which it is attached can give cyclic ethers, including epoxides. Although there is no definite limit to the size of J suitable for the processes of the invention, typically J comprises 1–100, more commonly 1–50, and most commonly 1–20 carbon atoms, and 0–25, more commonly 0–15 and most commonly 0–10 heteroatoms. The heteroatoms are commonly selected from halogen, oxygen, sulfur, nitrogen and phosphorus, and more commonly, halogen, oxygen, sulfur and nitrogen. Halogen includes fluorine, chlorine, bromine and iodine. Illustrative examples of the radical J are shown in Table 2.

TABLE 2

Examples of J groups useful in the methods of the invention

| | Chemical Structure |
|---|---|
| J-1 | —CH$_3$ |
| J-2 | —C(CH$_3$)$_3$ |
| J-3 | phenyl-Cl |
| J-4 | phenyl-NO$_2$ |
| J-5 | —(CH$_2$)$_2$-phenyl-OH |
| J-6 | —(CH$_2$)$_8$-phenyl-OH |
| J-7 | CH(CH$_3$)(phenyl)$_2$ |
| J-8 | CH(CH$_3$)(phenyl)(phenyl-Cl) |
| J-9 | (O$_2$N)-phenyl-S(O)$_2$CH$_3$ |
| J-10 | styryl |
| J-11 | decalin with CH$_3$ groups |
| J-12 | phenyl with OCH$_3$, OCH$_3$, O$_2$N substituents |
| J-13 | methylenedioxyphenyl with O$_2$N |

TABLE 2-continued

Examples of J groups useful in the methods of the invention

| | Chemical Structure |
|---|---|
| J-14 | (structure: bicyclic aromatic with CH₃ groups, SO₂, and dioxolane ring) |
| J-15 | CH₃-N=C(CH₃)₂ |
| J-16 | CH₂=CH-OCH₃ |

The linking group A in Formula 3 is also not directly involved in the acylation reaction center. Because the reaction conditions of the process of Scheme 1 are so mild, linking group A can accommodate a wide range of molecular structural features and all but the more reactive functionalities known to those skilled in the art. Therefore linking group A is best generally described as a linking group comprising an optionally substituted backbone segment consisting of 2 to 4 atoms selected from carbon atoms and 0 to 2 nitrogen, 0 to 2 oxygen and 0 to 2 sulfur atoms. More commonly, said optionally substituted backbone segment consists of 2 to 3 atoms selected from carbon atoms and 0 to 2 nitrogen, 0 to 1 oxygen and 0 to 1 sulfur atoms. Linking group A therefore completes with the 1,3-dione moiety (or an enolic tautomer of this moiety) an optionally substituted 5-, 6- or 7-membered carbocyclic or heterocyclic ring in Formulae 1 and 3. The 5-, 6- or 7-membered carbocyclic or heterocyclic ring is optionally fused with another optionally substituted carbocyclic or heterocyclic, saturated, partially unsaturated or aromatic, monocyclic or polycyclic ring system to form a polycyclic ring system. Some product compounds of interest include an optionally substituted benzene ring fused through linking group A to the ring comprising the 1,3-dione moiety (or an enolic tautomer of this moiety). As illustrated by compounds 3.7, 3.8, 3.9, 3.10 and 3.12 in Table 3 below, linking group A may contain a double or aromatic bond endocyclic to the ring containing the 1,3-dione moiety (or an enolic tautomer of this moiety), or linking group A may be fully saturated. Furthermore, linking group A may have one or more double or aromatic bonds exocyclic to the ring containing the 1,3-dione moiety (or an enolic tautomer of this moiety). The exocyclic double or aromatic bond may connect carbon or a heteroatom such as oxygen, sulfur or nitrogen, as exemplified by compounds 3.8, 3.9, 3.10 and 3.15 in Table 3 below. Optional substituents on linking group A including fused rings are independently selected from substitutents including, for example, alkyl, alkenyl, alkynyl, cycloalkyl, cycloalkenyl, cycloalkyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, aryloxy, alkylthio, alkenylthio, alkynylthio, alkylsulfinyl, alkenylsulfinyl, alkynylsulfinyl, arylsulfinyl, alkylsulfonyl, alkenylsulfonyl, alkynylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyloxy, alkenylaminocarbonyloxy, alkynylaminocarbonyloxy, arylaminocarbonyloxy, alkoxycarbonylamino, alkenyloxycarbonylamino, alkynyloxycarbonylamino and aryloxycarbonylamino, each further optionally substituted, and halogen, cyano and nitro. The optional further substituents are independently selected from groups like those illustrated above to give groups such as haloalkyl, haloalkenyl and haloalkoxy. The substituents may also be tied together by figuratively removing one to two hydrogen atoms from each of two substituents or a substituent and the supporting backbone and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH₂—O—. Tying together a hydroxy group and backbone to which it is attached can give cyclic ethers, including epoxides. Although there is no definite limit to the size of A suitable for the processes of the invention, typically A, including fused rings and substituents, comprises 1–50, more commonly 1–25, and most commonly 1–10 carbon atoms, and 0–10, more commonly 0–5 and most commonly 0–3 heteroatoms. The heteroatoms are commonly selected from halogen, oxygen, sulfur, nitrogen and phosphorus, and more commonly, halogen, oxygen, sulfur and nitrogen. Halogen includes fluorine, chlorine, bromine and iodine. Table 3 shows a variety of cyclic compounds illustrative of Formula 3.

TABLE 3

Examples of 1,3-Dicarbonyl Compounds shown in Formula 3

| | Chemical Structure |
|---|---|
| 3.1 | (cyclohexane-1,3-dione) |
| 3.2 | (5-methylcyclohexane-1,3-dione) |
| 3.3 | (5-carboxycyclohexane-1,3-dione, HOOC-substituted) |
| 3.4 | (5-phenylcyclohexane-1,3-dione) |

TABLE 3-continued

Examples of 1,3-Dicarbonyl Compounds shown in Formula 3

Chemical Structure

| | |
|---|---|
| 3.5 | |
| 3.6 | |
| 3.7 | |
| 3.8 | |
| 3.9 | |
| 3.10 | |
| 3.11 | |
| 3.12 | |
| 3.13 | |
| 3.14 | |
| 3.15 | |
| 3.16 | |

Methods for preparing phenyl esters of Formula 2 are well known in the art. For example, such methods are described in *Advanced Organic Chemistry*, 3rd Edition by J. March; John Wiley & Sons; New York (1985). These methods include palladium-catalyzed carbonylation of an aryl halide, usually an iodide, in the presence of a phenol. This method is illustrated in Examples 3A, 4A and 5A, which follow. As this method to prepare the phenyl ester is carried out in a basic environment, acid-sensitive groups on the J radical will not be degraded by the reaction conditions. The subsequent reaction of the phenyl ester with the 1,3-diketone, shown in Scheme 1, continues in a basic medium through which acid-sensitive groups will survive without decomposition.

Another route to phenyl esters is described by G. Satyanarayana and S. Sivaram in *Synthetic Communications* 1990, 20(21), 3273–6 in which, as is depicted in Scheme 2, phenyl esters of Formula 2a are produced by reaction in tetrahydrofuran solvent of Grignard reagents of Formula 4, which are in turn prepared from halides, with bis-phenyl carbonates such as Formula 5.

Scheme 2

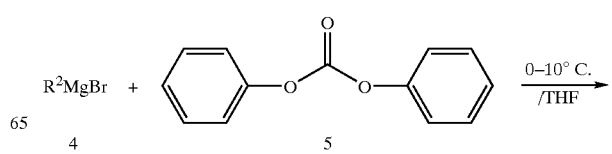

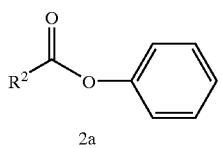

2a $R^2$ is, for example, ethyl, n-butyl, benzyl, phenyl or 4-methylphenyl. This route also can avoid acidic reaction conditions.

As reported by A. Rosowsky et al. in the *Journal of Medicinal Chemistry* 1985, 28(5), 660–67, phenyl esters of Formula 2 can be prepared by reaction of the appropriate carboxylic acids with bis-phenyl carbonates, again avoiding acidic conditions. A. Rosowsky et al. prepare the compound of Formula 2b by the treatment of the compound of Formula 6 with bis(p-nitrophenyl) carbonate in N,N-dimethylformamide (DMF) solvent.

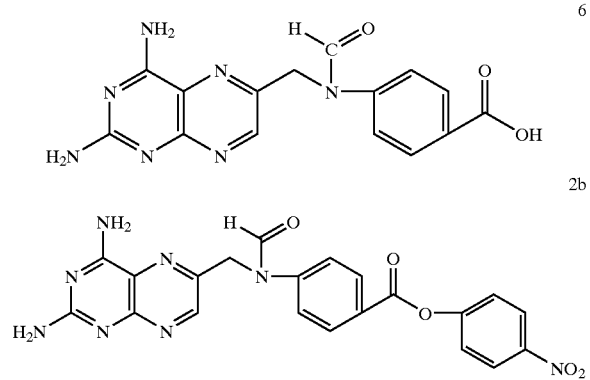

Acyl halide counterparts of Formula 2b needed for the prior art method of Scheme ii (i.e. Formula iv) cannot be prepared, because the acid chloride moiety would react with the amino groups.

When J does not include acid-sensitive substituents, other methods can be used to prepare phenyl esters of Formula 2. These include, for example, reaction of carboxylic acids with an inorganic halide such as thionyl chloride to form the corresponding acid chlorides, and then reacting the acid chlorides with the appropriate phenols. This method is reported in *Survey of Organic Syntheses*, Calvin A. Buehler and Donald E. Pearson, Wiley-Interscience (1970) and utilized in Example 8A, which follows. As yet another method, William H. Coppock in the *Journal of Organic Chemistry* 1957, 22, 325–26 reports preparing various substituted phenyl benzoates by Friedel-Crafts reaction of a substituted phenyl chloroformate with alkylbenzenes or arylbenzenes using aluminum chloride catalyst. These last two methods are useful for preparing phenyl benzoates of Formula 2 when there are no acid sensitive groups on the J radical.

General methods for preparing cyclic compounds of Formula 3 are well known in the art, see, for example, Volume 13, page 929 of the Kirk-Othmer *Encyclopedia of Chemical Technology*, John Wiley & Sons. Five and six membered cyclic 1,3-diketones (including their enolic tautomers) can be prepared by either treating corresponding γ-keto acids with concentrated sulfuric acid, or keto esters with base. For example, treating ethyl levulinate ($CH_3C(O)(CH_2)_2CO_2C_2H_5$) with sodium hydroxide in ethanol produces 1,3-cyclo-pentanedione. Sections 12.47 and 13.11 of *Advanced Organic Chemistry* by Louis F. and Mary Fieser, Reinhold 1961 show two additional methods for synthesis of 1,3-diketones. In the first, 1,3-cyclohexanedione is prepared by hydrogenation of 1,3-dihydroxybenzene using Raney nickel in aqueous alkali. In another example, a substituted 1,3-cyclohexanedione is made by base-catalyzed condensation of an α,β-unsaturated ester with a gem di(alkoxycarbonyl)alkane. The resulting enolate is heated with aqueous alkali hydroxide to hydrolyze the ester group and, on acidification, the β-keto acid loses carbon dioxide to produce the substituted 1,3-cyclohexanedione. As an example, 5,5-dimethylcyclohexane-1,3-dione was produced in this way from diethyl 1,3-propandioate and 4-methyl-3-penten-2-one; see also R. L. Shriner and H. R. Todd, *Org. Syn.*, Coll. Vol. 2, 200 (1943).

A particular advantage of the method of this invention is that acylation is carried out using a phenyl ester instead of the acyl chloride of the prior art methods. Any J substituent which is acid-sensitive or reactive with an acyl chloride can lead to decomposition and yield loss using the prior art method. The method of the present invention (Scheme 1) avoids this limitation by using phenyl esters instead of acyl halides as acylating agents. For example, an attempt was made to use the prior art method to prepare the product later successfully prepared in Example 3A using the method of the present invention. Using the prior art method required first preparing the acid chloride of Formula 9 from the corresponding carboxylic acid of Formula 7 by treatment with thionyl chloride (8) as shown in Scheme 3.

Scheme 3

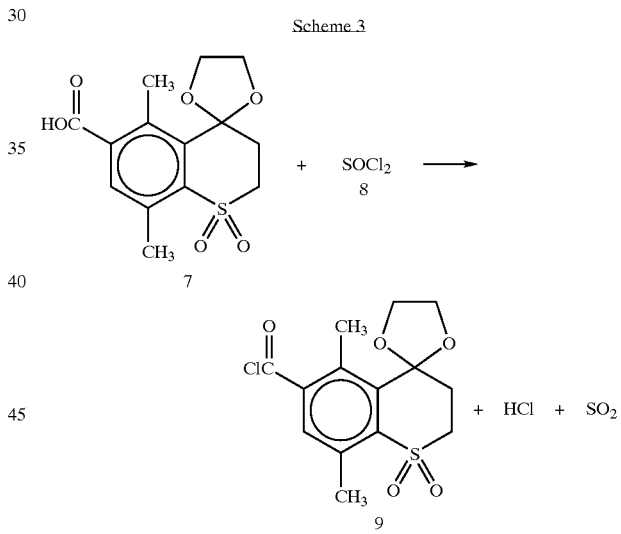

Under normal commercial process conditions and hold times the dioxolane group in Formula 9 was not stable in the acid environment required in its production, and the resulting yield loss made the prior art approach impractical. The process of this invention proved superior because no acid chloride is required. Other acid-sensitive groups, which would also make the prior art method impractical, include vinyl ethers, acetals, ketals, epoxides, hydrazones, imines, carbamates and amides. Examples of such groups are shown in Table 2, structures J-13 through J-16.

Without further elaboration, it is believed that by means of the preceding description one skilled in the art can utilize the present invention to its fullest extent. The following examples are, therefore, to be construed as merely illustrative and not limiting of the disclosure in any way whatsoever.

EXAMPLE 1

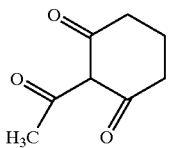

Preparation of 2-Acetyl-1,3-cyclohexanedione

A 200-mL 2-necked round bottom flask was fitted with thermometer, reflux condenser, magnetic stirrer, and nitrogen bypass. The flask was charged with 4.53 g (25 mmol) of 4-nitrophenyl acetate, 2.94 g (26.25 mmol) of 1,3-cyclohexanedione, 5.69 g (56.25 mmol) of triethylamine, 0.22 g (2.5 mmol) of acetone cyanohydrin, and 60 mL of acetonitrile. The mixture was heated to reflux with stirring for 3 hr. The mixture was allowed to cool to room temperature and volatiles were removed under reduced pressure to give 20.0 g of red oil. Chromatographic separation on silica gel afforded the title product. $^1$H NMR (CDCl$_3$): δ 1.99 (m, 2), 2.52 (m, 2), 2.62 (s, 3), 2.68 (m, 2).

EXAMPLE 2

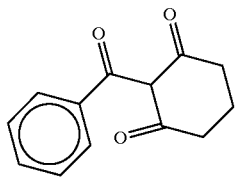

Preparation of 2-Benzoyl-1,3-cyclohexanedione

The apparatus, reagents and amounts of Example 1 were used with 6.08 g (25 mmol) of 4-nitrophenyl benzoate used in place of 4-nitrophenyl acetate. The mixture was heated to reflux with stirring for 5 hr. It was allowed to cool to room temperature and volatiles were removed under reduced pressure to give the title product as 11.84 g of red oil. $^1$H NMR (CDCl$_3$): δ 2.08 (m, 2), 2.48 (m, 2), 2.72 (m, 2), 7.40 (m, 2), 7.52 (m, 3).

EXAMPLE 3A

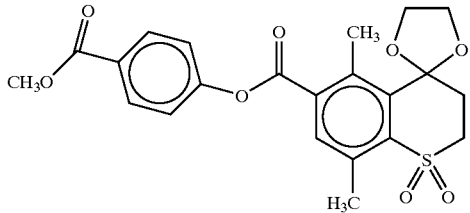

Preparation of 4-(methoxycarbonyl)phenyl 2,3-dihydro-5,8-dimethylspiro[4H-1-benzothiopyran-4,2'-[1,3]dioxolane]-6-carboxylate 1,1-dioxide A Fisher-Porter tube* was charged with 3.94 g (10 mmol) of 2,3-dihydro-6-iodo-5,8-dimethylspiro[4H-1-benzothiopyran-4,2'-[1,3]dioxolane] 1,1-dioxide, 1.67 g (11 mmol) of methyl 4-hydroxybenzoate, 2.28 g (22.5 mmol) of triethylamine, 23 mg (0.1 mmol) of palladium acetate, and 20 mL of dry N,N-dimethylformamide (DMF). The mixture was heated for 2.5 hr at 80° C. in a carbon monoxide atmosphere at 70 psi (4.8×10$^5$ Pa). The mixture was cooled to room temperature and filtered through Celite® diatomaceous earth filter aid into 150 mL of stirred ice water. The Celite® was rinsed with 10 mL of DMF, which was added to the ice water. The resulting precipitate was collected by filtration, washed with 25 mL of water, 15 mL of acetonitrile, 20 mL of diethyl ether and allowed to dry to give 4.20 g of the title product as a pale pink solid, m.p. 206–208° C. $^1$H NMR (CDCl$_3$): δ 2.57 (s, 3), 2.58 (m, 2), 2.82 (s, 3), 3.52 (m, 2), 3.94 (s, 3), (s, 3), 4.20 (m, 2), 4.34 (m 2), 7.30 (m, 2), 7.79 (s, 1), 8.14 (m, 2).

* A Fisher-Porter tube is a thick walled test tube fitted through a gasket to a pressure gauge and associated valving to enable reactions above atmospheric pressure to be conducted.

EXAMPLE 3B

Preparation of 2-[(2,3-dihydro-5,8-dimethyl-1,1-dioxidospiro[4H-1-benzothiopyran-4,2'-[1,3]dioxolan]-6-yl)carbonyl]-3-hydroxy-2-cyclohexen-1-one triethylamine from 4-(methoxycarbonyl)phenyl 2,3-dihydro-5,8-dimethylspiro[4H-1-benzothiopyran-4,2'-[1,3]dioxolane]-6-carboxylate 1,1-dioxide A 300-mL 1-necked round bottom flask was fitted with magnetic stirrer and reflux condenser with balloon on top of the condenser. The flask was charged with 8.93 g (20 mmol) of 4-(methoxycarbonyl)phenyl 2,3-dihydro-5,8-dimethylspiro[4H-1-benzothio-pyran-4,2'-[1,3]dioxolane]-6-carboxylate 1,1-dioxide, 2.47 g (22 mmol) of 1,3-cyclohexane-dione, 5.05 g (50 mmol) of triethylamine, 0.20 g (3 mmol) of potassium cyanide, and 50 mL of acetonitrile. The mixture was heated for 6 hr at reflux. It was allowed to cool to room temperature, and then cooled to 5° C. Solids were collected by filtration, washed twice with 15 mL portions of acetonitrile and allowed to dry to give 8.26 g of the title product as white solid, m.p. 205–206° C. $^1$H NMR (CDCl$_3$): δ 1.17 (t, 9), 1.94 (m, 2), 2.23 (s, 3), 2.44 (t, 4), 2.56 (m, 2), 2.69 (s, 3), 2.93 (q, 6), 3.43 (m, 2), 4.18 (m, 4), 6.90 (s, 1). Analysis by HPLC indicated the filtrate contained an additional 1.16 g of product.

EXAMPLE 4A

Preparation of 2-(methoxycarbonyl)phenyl 2,3-dihydro-5,8-dimethylspiro[4H-1-benzothiopyran-4,2'-[1,3]dioxolane]-6-carboxylate 1,1-dioxide A Fisher-Porter tube (defined in Example 3A) was charged with 3.94 g (10 mmol) of 2,3-dihydro-6-iodo-5,8-dimethylspiro[4H-1-benzothiopyran-4,2'-[1,3]dioxolane] 1,1-dioxide, 1.53 g (15 mmol) of triethylamine, 23 mg (0.1 mmol) of palladium acetate, 1.67 g (11 mmol) of methyl salicylate, and 20 mL of DMF. The mixture was heated for 3 hr at 80° C. followed by 17 hr at 50° C. in a carbon monoxide atmosphere at 70 psi (4.8×10$^5$ Pa). The mixture was poured into 150 mL of ice water and filtered. The solid was washed with 10 mL of water, 10 mL of acetonitrile, and 10 mL of diethyl ether to give the title product as 3.50 g of pink solid, m.p. 179–181° C. $^1$H NMR (CDCl$_3$): δ 2.58 (s, 3), 2.60 (m, 2), 2.84 (s, 3), 3.52 (m, 2), 3.84 (s, 3), 4.19 (m, 2), 4.34 (m, 2), 7.20 (d, 1), 7.36 (t, 1), 7.61 (t, 1), 8.02 (s, 1), 8.08 (d, 1).

EXAMPLE 4B

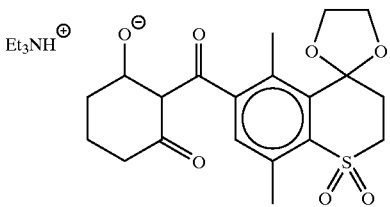

Preparation of 2-[(2,3-dihydro-5,8-dimethyl-1,1-dioxidospiro[4H-1-benzothiopyran-4,2'-[1,3]dioxolan]-6-yl)carbonyl]-3-hydroxy-2-cyclohexen-1-one triethylamine from 2-(methoxycarbonyl)phenyl 2,3-dihydro-5,8-dimethylspiro[4H-1-benzothiopyran-4,2'-[1,3]dioxolane]-6-carboxylate 1,1-dioxide A Fisher-Porter tube (defined in Example 3A) was charged with 3.34 g (7.5 mmol) of 2-(methoxycarbonyl)-phenyl 2,3-dihydro-5,8-dimethylspiro[4H-1-benzothiopyran-4,2'-[1,3]dioxolane]-6-carboxylate 1,1-dioxide, 0.93 g (8.25 mmol) of 1,3-cyclohexanedione, 1.70 g (17 mmol) of triethylamine, 49 mg (0.75 mmol) of potassium cyanide and 18 mL of acetonitrile. The mixture was heated for 10 hr at 90° C. It was allowed to cool to room temperature and filtered. The solid was washed with 6 mL of acetonitrile and allowed to dry under a stream of nitrogen to give the title product as 3.23 g of off-white solid, m.p. 203–205° C.

EXAMPLE 5A

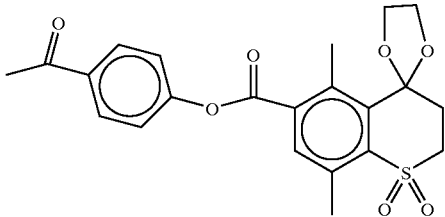

Preparation of 4-acetylphenyl 2,3-dihydro-5,8-dimethylspiro[4H-1-benzothiopyran-4,2'-[1,3]dioxolane]-6-carboxylate 1,1-dioxide A Fisher-Porter tube (defined in Example 3A) was charged as in Example 4A using 1.50 g (11 mmol) of 4-hydroxyacetophenone in place of methyl salicylate. The mixture was heated for 3 hr at 80° C. It was worked up as in Example 4A to give the title product as 4.15 g of pale pink solid, m.p. 224–226° C. $^1$H NMR (CDCl$_3$): δ 2.57 (s, 3), 2.60 (m, 2), 2.63 (s, 3), 2.82 (s, 3), 3.52 (m, 2), 4.20 (m, 2), 4.34 (m, 2), 7.31 (m, 2), 7.80 (s, 1), 8.06 (m, 2).

EXAMPLE 5B

Preparation of 2-[(2,3-dihydro-5,8-dimethyl-1,1-dioxidospiro[4H-1-benzothiopyran-4,2'-[1,3]dioxolan]-6-yl)carbonyl]-3-hydroxy-2-cyclohexen-1-one triethylamine from 4-acetylphenyl 2,3-dihydro-5,8-dimethylspiro[4H-1-benzothiopyran-4,2'-[1,3]dioxolane]-6-carboxylate 1,1-dioxide A 100-mL 2-necked round bottom flask was fitted with thermometer, reflux condenser with nitrogen bypass, and magnetic stirrer. The flask was charged with 1.08 g (2.5 mmol) of 4-acetylphenyl 2,3-dihydro-5,8-dimethylspiro[4H-1-benzothiopyran-4,2'-[1,3]dioxolane]-6-carboxylate 1,1-dioxide, 0.30 g (2.63 mmol) of 1,3-cyclohexanedione, 0.63 g (6.25 mmol) of triethylamine, 10 mL of acetonitrile, and 21 mg (0.25 mmol) of acetone cyanohydrin. The mixture was heated to reflux with stirring for 5 hours. It was stirred for 67 hr at 23° C. It was then heated at 80° C. for 2 hr after which 0.126 g of triethylamine was added followed by 3 hr at 80° C. The mixture was then stirred at 23° C. for 17 hr after which it was heated to 79° C. At 110 hr, 0.21 g of triethylamine and 21 mg of acetone cyanohydrin were added. Heating was continued for an additional 16 hr. The mixture was allowed to cool to room temperature and filtered. The solid was washed with 2 mL of acetonitrile, and allowed to dry under a stream of nitrogen to give the title product as 1.04 g of white solid, m.p. 205–206° C.

EXAMPLE 6

Preparation of 2-[(2,3-dihydro-5,8-dimethyl-1,1-dioxidospiro[4H-1-benzothiopyran-4,2'-[1,3]dioxolan]-6-yl)carbonyl]-1,3-cyclohexanedione from 2-nitrophenyl 2,3-dihydro-5,8-dimethylspiro[4H-1-benzothiopyran-4,2'-[1,3]dioxolane]-6-carboxylate 1,1-dioxide using Potassium Fluoride A 50-mL 2-necked round bottom flask was fitted with thermometer, magnetic stirrer, and distillation head. The flask was charged with 1.10 g (2.5 mmol) of 2-nitrophenyl 2,3-dihydro-5,8-dimethylspiro[4H-1-benzothiopyran-4,2'-[1,3]dioxolane]-6-carboxylate 1,1-dioxide, 0.31 g (2.75 mmol) of 1,3-cyclohexanedione, 0.58 g (10 mmol) of spray-dried potassium fluoride, 2 mL of acetonitrile, and 11 mL of methyl sulfoxide (alternatively named dimethyl sulfoxide). The pressure was reduced with a water aspirator and 3 mL of distillate was removed at a distillation temperature of 69° C. The distillation head was replaced with a reflux condenser and the mixture was heated for 2 hr at 80° C. The mixture was allowed to cool to room temperature and dissolved in aqueous acetonitrile. Quantitative analysis of this solution by HPLC indicated an 85% yield of the title product.

EXAMPLE 7A

Preparation of the Potassium Salt of 1,3-cyclohexanedione

A 100-mL 2-necked round bottom flask was charged with 4.62 g (40 mmol) of 1,3-cyclohexanedione, 2.64 g (40 mmol) of 85% potassium hydroxide, 5 mL of water, and 50 mL of toluene. The mixture was heated to reflux and water was removed as an azeotrope until only toluene distilled over. The mixture was cooled to room temperature and filtered. The solid was dried under vacuum at room temperature to give the title product as 5.95 g of pale yellow solid, m.p. 247–250° C.

EXAMPLE 7B

Preparation of 2-[(2,3-dihydro-5,8-dimethyl-1,1-dioxidospiro[4H-1-benzothiopyran-4,2'-[1,3]dioxolan]-6-yl)carbonyl]-1,3-cyclohexanedione from 4-(methoxycarbonyl)phenyl 2,3-dihydro-5,8-dimethylspiro[4H-1-benzothiopyran-4,2'-[1,3]dioxolane]-6-carboxylate 1,1-dioxide and the Potassium Salt of 1,3-cyclohexanedione A Fisher-Porter tube (defined in Example 3A) was charged with 1.67 g (3.7 mmol) of 4-(methoxycarbonyl)

phenyl 2,3-dihydro-5,8-dimethylspiro[4H-1-benzothiopyran-4,2'-[1,3]-dioxolane]-6-carboxylate 1,1-dioxide, 0.62 g of the product of Example 7A, 26 mg (0.4 mmol) of potassium cyanide, and 10 mL of acetonitrile. The mixture was heated for 19 hr at 80° C. Quantitative analysis of the reaction mixture by HPLC indicated the presence of the title product in 93% yield.

EXAMPLE 8A

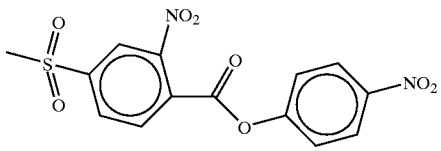

Preparation of 4-nitrophenyl 2-nitro-4-(methylsulfonyl)benzoate

A 100-mL 2-necked round bottom flask was fitted with thermometer, magnetic stirrer, and reflux condenser with nitrogen bypass. The flask was charged with 1.23 g (5 mmol) of 2-nitro-4-(methylsulfonyl)benzoic acid, 2 drops of DMF, and 20 mL of dichloromethane. Oxalyl chloride (0.70 g, 5.5 mmol) was added dropwise and the mixture was stirred for 1 hr. A solution consisting of 0.70 g (5 mmol) of 4-nitrophenol, 0.55 g (5.5 mmol) of triethylamine and 5 mL of dichloromethane was added and the mixture was stirred for 1 hr. The mixture was diluted with 100 mL of dichloromethane, washed twice with 100 mL portions of aqueous sodium bicarbonate, once with 100 mL of water, dried with magnesium sulfate, filtered, and volatiles removed under reduced pressure to give the title product as 1.56 g of off-white solid, m.p. 171–173° C. $^1$H NMR (CDCl$_3$): δ 3.19 (s, 3), 7.47 (m, 2), 8.10 (m, 1), 8.38 (m, 3), 8.69 (m, 1).

EXAMPLE 8B

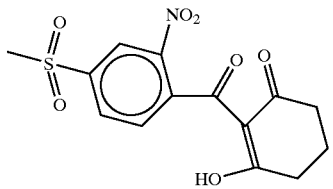

Preparation of 3-hydroxy-2-[4-(methylsulfonyl)-2-nitrobenzoyl]-2-cyclohexen-1-one A 100-mL 2-necked round bottom flask was fitted with thermometer, magnetic stirrer, and reflux condenser with nitrogen bypass. The flask was charged with 1.10 g (3 mmol) of 4-nitrophenyl 2-nitro-4-(methylsulfonyl)benzoate, 0.37 g (3.3 mmol) 1,3-cyclohexanedione, 0.76 (75 mmol) of triethylamine, 26 mg (0.3 mmol) of acetone cyanohydrin, and 10 mL of acetonitrile. The mixture was stirred for 1 hr at 22° C. It was poured into 200 mL of dilute aqueous sodium bicarbonate, washed once with diethyl ether, once with ethyl acetate, and acidified with hydrochloric acid. It was extracted with 200 mL of dichloromethane, which was then dried over magnesium sulfate and filtered. Volatiles were removed under reduced pressure to give 1.20 g of oil. The oil was washed with 200 mL of hot water and triturated with diethyl ether to give the title product as 0.22 g of white solid, m.p. 158° C. (decomposes). $^1$H NMR (CDCl$_3$): δ 2.06 (m, 2), 2.37 (m, 2), 2.82 (m, 2), 3.16 (s, 3), 7.45 (d, 1), 8.24 (d, 1), 8.76 (s,1).

EXAMPLE 9A

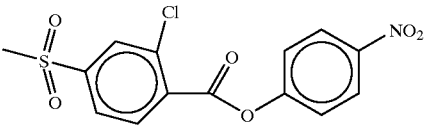

Preparation of 4-nitrophenyl 2-chloro-4-(methylsulfonyl)benzoate

A 200-mL round bottom flask was fitted with thermometer, magnetic stirrer, and reflux condenser with nitrogen bypass. The flask was charged with 0.94 g (4 mmol) of 2-chloro-4-(methylsulfonyl)benzoic acid, 2 drops of DMF, and 20 mL of dichloromethane. Oxalyl chloride (0.56 g, 4.4 mmol) was added dropwise and the mixture was stirred for 1 hr. A solution consisting of 0.62 g (4 mmol) of 4-nitrophenol, 0.44 g (4.4 mmol) of triethylamine and 5 mL of dichloromethane was added slowly. The mixture was stirred for 1 hr, diluted with 100 mL of dichloromethane, washed twice with 100 mL portions of dilute aqueous sodium bicarbonate, once with water, dried over magnesium sulfate, filtered, and volatiles removed under reduced pressure to give the title product as 1.30 g of off-white solid, m.p. 123–125° C. $^1$H NMR (CDCl$_3$): δ 3.14 (s, 3), 7.48 (m, 2), 8.00 (m, 1), 8.14 (m, 1), 8.21 (m, 1), 8.36 (m, 2).

EXAMPLE 9B

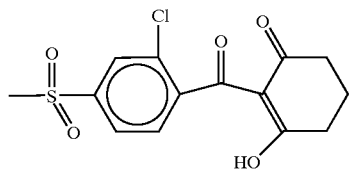

Preparation of 2-[2-chloro-4-(methylsulfonyl) benzoyl]-3-hydroxy-2-cyclohexen-1-one A 100-mL 2-necked round bottom flask was fitted with thermometer, magnetic stirrer, and reflux condenser with nitrogen bypass. The flask was charged with 1.06 g (3 mmol) of 4-nitrophenyl 2-chloro-4-(methylsulfonyl)benzoate, 0.37 g (3.3 mmol) of 1,3-cyclohexanedione, 0.76 g (7.5 mmol) of triethylamine, 26 mg (0.3 mmol) of acetone cyanohydrin, and 10 mL of acetonitrile. The mixture was stirred for 3 hr at 22° C. It was worked up as in Example 8B to give 1.26 g of yellow oil. Treatment of the oil as in Example 8B gave the title product as 0.35 g of white solid, m.p. 141–142° C. $^1$H NMR (CDCl$_3$): δ 2.08 (m, 2), 2.46 (m, 2), 2.82 (m, 2), 3.09 (s, 3), 7.37 (d, 1), 7.88 (d, 1), 7.96 (s, 1).

EXAMPLES 10–36

Examples 10–36 of the process were carried out as shown in Scheme 4 and listed in Table 4, using the following methods:

Method (A) Ester 2c (2.3 mmol) and dione 3b (2.7 mmol), were combined in (methyl sulfoxide)-d$_6$ (abbreviated DMSO-d$_6$) (5.0 g) and the mixture was heated to 80° C. Potassium fluoride (0.60 g, 10 mmol) was added in a single portion and the mixture was stirred at 80° C. The progress of the reaction was followed by NMR of aliquots until the ester was >98% converted to phenol, or until no further progress was observed. Completed reactions were worked up by partitioning the cooled reaction mixture between water (25 mL) and diethyl ether (25 mL). The organic layer was washed with water (3×5 mL) and brine (5 mL), dried over magnesium sulfate, filtered, and volatiles were evaporated. The product could be isolated by flash chromatography over silica gel**.

** The elution solvents were binary mixtures of hexanes, ethyl acetate, methylene chloride and 2-propanol; the choice of solvents and ratios dependent on the polarity of the product to be purified. See the footnotes below the table for specific solvents and ratios.

Method (B) Ester 2c (11.2 mmol) and dione 3b (15 mmol) were combined in acetonitrile (15 mL). Triethylamine (2.5 g, 25 mmol) and acetone cyanohydrin (0.14 mL, 1.5 mmol) were added and the mixture was heated to reflux. The progress of the reaction was followed by NMR of aliquots until the ester was >98% converted to phenol, or until no further progress was observed. Completed reactions were worked up by evaporating volatiles and partitioning the residue between diethyl ether and saturated aqueous sodium bicarbonate solution. The aqueous solution was acidified with 1N aqueous hydrochloric acid and the product was isolated by filtration (if solid) or extraction into dichloromethane. After concentration of the dichloromethane solution, liquid products could be further purified by flash chromatography over silica gel**.

** The elution solvents were binary mixtures of hexanes, ethyl acetate, methylene chloride and 2-propanol; the choice of solvents and ratios dependent on the polarity of the product to be purified. See the footnotes below the table for specific solvents and ratios.

Method (C) Same as Method B except that potassium cyanide (100 mg, 1.5 mmol) was used as the catalyst in place of acetone cyanohydrin.

TABLE 4

SCHEME 4

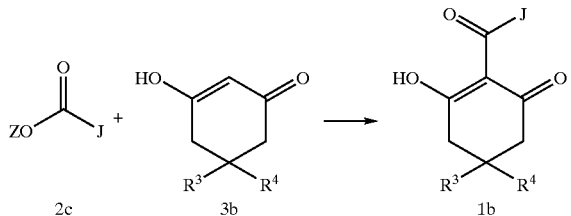

Examples 10–36

| Ex. # | $R^3$ | $R^4$ | J | Z | Method | Time | Conversion (%)[a] | Isolated Yield (%) |
|---|---|---|---|---|---|---|---|---|
| 10 | H | H | $CH_3$ | $4\text{-}O_2NC_6H_4\text{—}$ | A | 2 hr | >98 | |
| 11 | H | H | $CH_3$ | $2\text{-}O_2NC_6H_4\text{—}$ | A | 1 hr | >98 | |
| 12 | $CH_3$ | $CH_3$ | $CH_3$ | $4\text{-}O_2NC_6H_4\text{—}$ | A | 1 hr | >98 | 76[b] |
| 13 | $CH_3$ | $CH_3$ | $CH_3$ | $2\text{-}O_2NC_6H_4\text{—}$ | A | 1 hr | >98 | |
| 14 | $C_6H_5$ | H | $CH_3$ | $2\text{-}O_2NC_6H_4\text{—}$ | A | 8 hr | >98 | 47[c] |
| 15 | $C_6H_5$ | H | $CH_3$ | $4\text{-}O_2NC_6H_4\text{—}$ | A | 8 hr | >98 | |
| 16 | $CH_3$ | $CH_3$ | $CH_3$ | $4\text{-}MeO_2CC_6H_4\text{—}$ | A | 21 hr | 81 | |
| 17 | $CH_3$ | $CH_3$ | $CH_3$ | $4\text{-}O_2NC_6H_4\text{—}$ | C[d] | 2 hr | ~98 | |
| 18 | $CH_3$ | $CH_3$ | $CH_3$ | $4\text{-}MeO_2CC_6H_4\text{—}$ | C[d,e] | 6 hr | 93 | |
| 19 | $CH_3$ | $CH_3$ | $CH_3$ | $4\text{-}O_2NC_6H_4\text{—}$ | B[d,f] | 4 hr | >98 | |
| 20 | $CH_3$ | $CH_3$ | $CH_3$ | $4\text{-}MeO_2CC_6H_4\text{—}$ | B[d] | 20 hr | 94 | |
| 21 | $CH_3$ | $CH_3$ | $CH_3$ | $4\text{-}MeO_2CC_6H_4\text{—}$ | B | 4 hr | 95 | |
| 22 | $CH_3$ | $CH_3$ | $4\text{-}CH_3C_6H_4$ | $4\text{-}NCC_6H_4\text{—}$ | A | 8 hr | >98 | 73[g] |
| 23 | $CH_3$ | $CH_3$ | $C_6H_5$ | $4\text{-}MeO_2CC_6H_4\text{—}$ | A | 12 hr | >98 | 73[h] |
| 24 | $CH_3$ | $CH_3$ | $C_9H_{19}\text{-}n$ | $3\text{-}O_2NC_6H_4\text{—}$ | A | 4 hr | >98 | 86[i] |
| 25 | $CH_3$ | $CH_3$ | $3\text{-}ClC_6H_4$ | $4\text{-}O_2NC_6H_4\text{—}$ | A | 2 hr | >98 | 76[j] |
| 26 | $CH_3$ | $CH_3$ | $3\text{-}ClC_6H_4$ | $4\text{-}O_2NC_6H_4\text{—}$ | B | 2 hr | >98 | 76[k] |
| 27 | $CH_3$ | $CH_3$ | $3\text{-}ClC_6H_4$ | $4\text{-}O_2NC_6H_4\text{—}$ | C | 2 hr | >98 | 91[l] |
| 28 | $CH_3$ | $CH_3$ | $4\text{-}CH_3C_6H_4$ | $4\text{-}NCC_6H_4\text{—}$ | C | 6 hr | 97 | 89[m] |
| 29 | $C_6H_5$ | H | $3\text{-}ClC_6H_4$ | $4\text{-}O_2NC_6H_4\text{—}$ | A | 4 hr | >98 | 45[n] |
| 30 | $C_6H_5$ | H | $4\text{-}CH_3C_6H_4$ | $4\text{-}NCC_6H_4\text{—}$ | A | 22 hr | 96 | 53[o] |
| 31 | $CH_3$ | $CH_3$ | $4\text{-}CH_3C_6H_4$ | $4\text{-}NCC_6H_4\text{—}$ | B | 7 hr | 96 | 87[p] |
| 32 | $CH_3$ | $CH_3$ | $C_6H_5$ | $4\text{-}MeO_2CC_6H_4\text{—}$ | B | 22 hr | 93 | 84[q] |
| 33 | $CH_3$ | $CH_3$ | $C_6H_5$ | $4\text{-}MeO_2CC_6H_4\text{—}$ | C | 6 hr | 96 | 87[r] |
| 34 | $4\text{-}ClC_6H_4$ | H | $3\text{-}ClC_6H_4$ | $4\text{-}O_2NC_6H_4\text{—}$ | B | 2 hr | >98 | 81[s] |
| 35 | $4\text{-}ClC_6H_4$ | H | $3\text{-}ClC_6H_4$ | $4\text{-}O_2NC_6H_4\text{—}$ | C | 2 hr | >98 | 76[t] |
| 36 | H | H | $4\text{-}CH_3C_6H_4$ | $4\text{-}NCC_6H_4\text{—}$ | B | 6 hr | 94 | 41[u] |

[a]Determined by the phenol:phenyl ester ratio in the NMR spectrum of an aliquot.
[b]Pale yellow oil. $^1$NMR(CDCl$_3$): δ 1.08(s, 6), 2.36(m, 2), 2.54(m, 2), 2.61(s, 3). Flash chromatography solvent was hexanes:ethyl acetate (9:1).
[c]Fluffy white solids, m.p. 99–101° C. (hexanes). $^1$NMR(CDCl$_3$): δ 2.64(s, 3), 2.74(m, 2), 2.90(m, 2), 3.37(m, 1), 7.24(m, 3), 7.35(m, 2). Flash chromatography solvent was hexanes:ethyl acetate (4:1).
[d]Used 12.5 mmol of the starting dione and used 25 mL of acetonitrile as solvent.
[e]Added another 100 mg (1.5 mmol) of potassium cyanide after 2 hours refluxing.
[f]Added an additional 2.5 mmol of starting dione after 3 hours refluxing.
[g]Off-white powder, m.p. 121–124° C. $^1$NMR(CDCl$_3$): δ 1.15(s, 6), 2.39(m, 2), 2.40(s, 3), 2.62(m, 2), 7.19(d, 2), 7.43(d, 2).

TABLE 4-continued

SCHEME 4

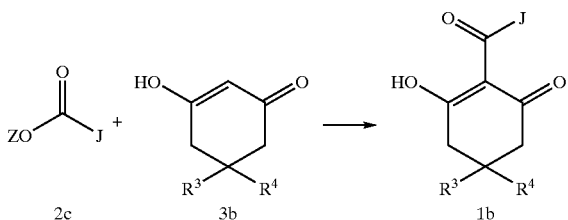

Examples 10–36

| Ex. # | R³ | R⁴ | J | Z | Method | Time | Conversion (%)[a] | Isolated Yield (%) |
|---|---|---|---|---|---|---|---|---|

[h]Off-white powder, m.p. 116–117° C. ¹NMR(CDCl₃): δ 1.15(s, 6), 2.39(m, 2), 2.64(m, 2), 7.40(m, 2), 7.49(m, 3).
[i]Yellow oil. ¹NMR(CDCl₃): δ 0.88(t, 3), 1.08(s, 6), 1.2–1.4(m, 12), 1.61(m, 2), 2.35(m, 2), 2.53(m, 2), 3.02(dd, 2).
[j]Off-white crystals, m.p. 87–91° C. ¹NMR(CDCl₃): δ 1.15(s, 6), 2.39(m, 2), 2.65(m, 2), 7.32(m, 2), 7.46(m, 2). Flash chromatography solvent was hexanes:ethyl acetate(9:1).
[k]Off-white powder, m.p. 88–91° C.
[l]Off-white powder, m.p. 87–90° C.
[m]Pale yellow powder, m.p. 125–127° C.
[n]Tan powder, m.p. 89–91° C. (hexanes-diethyl ether). ¹NMR(CDCl₃): δ 2.65–2.85(m, 2), 3.01(m, 2), 3.48(m, 1), 7.25–7.45(m, 7), 7.48(m, 2).
[o]Tan powder, m.p. 101–107° C. (hexanes-chlorobutane). ¹NMR(CDCl₃): δ 2.40(s, 3), 2.6–2.9(m, 2), 3.00(m, 2), 3.49(m, 1), 7.20–7.35(m, 5), 7.37(m, 2), 7.48(d, 2). Flash chromatography solvent was dichloromethane:2-propanol (19:1).
[p]Pale yellow powder, m.p. 126–128° C. Flash chromatography solvent was dichloromethane:2-propanol (19:1).
[q]Pale yellow powder, m.p. 115–117° C.
[r]Off-white powder, m.p. 116–118° C.
[s]Pale yellow powder, m.p. 101–103° C. (hexanes-diethyl ether). ¹NMR(CDCl₃): δ 2.6–3.1(m, 4), 3.47(m, 1), 7.20(d, 2), 7.35(m, 4), 7.48(m, 2).
[t]Pale yellow powder, m.p. 91–101° C. (hexanes-diethyl ether).
[u]Light yellow solids, m.p. 67–70° C. (hexanes). ¹H NMR(CDCl₃): δ 2.07(m, 2), 2.39(s, 3), 2.50(t, 2), 2.73(t, 2), 7.19(d, 2), 7.44(d, 2). Flash chromatography solvent was dichloromethane:ethyl acetate (9:1).

EXAMPLE 37

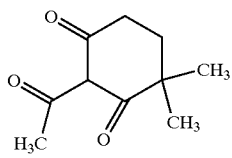

Preparation of 2-Acetyl-4,4-dimethyl-1,3-cyclohexanedione

A 50-mL single neck round bottom flask was charged with 4-nitrophenyl acetate (2.03 g, 11.2 mmol), 4,4-dimethyl-1,3-cyclohexanedione (2.10 g, 15 mmol) and acetonitrile (15 mL). Then triethylamine (2.5 g, 25 mmol) and acetone cyanohydrin (0.14 mL, 1.5 mmol) were added and the mixture was stirred for 2 hours at ambient temperature. NMR analysis of an aliquot showed that 43% of the starting acetate was still unreacted. The mixture was then refluxed for 2 hours after which time NMR analysis of an aliquot showed no starting acetate remaining.

Volatiles were stripped from the reaction mixture and the residue was partitioned between diethyl ether (100 mL) and 1N hydrochloric acid (50 mL). The organic layer was washed with brine (25 mL), dried over magnesium sulfate, filtered and stripped to a brown oil (3.78 g). This oil was chromatographed on silica gel (200 g), eluting with hexanes-ethyl acetate (9:1). Concentration of the fractions containing pure product afforded the title compound as a yellow oil, 1.41 g (69.1%). ¹H NMR (CDCl₃): δ 1.16 (s, 3), 1.30 (s, 3), 1.83 (m, 2), 2.54 (m, 1), 2.60 (s, 3), 2.69 (m, 1).

EXAMPLE 38

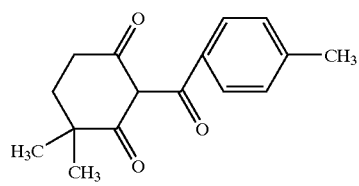

Preparation of 2-(4-Methylbenzoyl)-4,4-dimethyl-1,3-cyclohexanedione

A 50-mL single neck round bottom flask was charged with 4-cyanophenyl 4-methylbenzoate (2.65 g, 11.2 mmol), 4,4-dimethyl-1,3-cyclohexanedione (2.10 g, 15 mmol) and acetonitrile (15 mL). Then triethylamine (2.5 g, 25 mmol) and acetone cyanohydrin (0.14 mL, 1.5 mmol) were added and the mixture was refluxed for 6 hours. Volatiles were stripped from the reaction mixture and the residue was partitioned between diethyl ether (100 mL) and water (50 mL). The organic layer was extracted with saturated aqueous sodium bicarbonate (30 mL), then water (10 mL), then brine (10 mL). All aqueous layers were combined and 1N hydrochloric acid was added to pH 1. The resulting oil was extracted into dichloromethane (30 mL, 2×15 mL). The dichloromethane layers were combined, dried over magnesium sulfate, filtered and stripped to a brown oil (3.57 g). The crude product was chromatographed on silica gel (200 g), eluting with hexanes-ethyl acetate (4:1). Fractions containing pure product were concentrated to a yellow oil (2.08 g), which was crystallized from hexanes to afford the title compound as off-white crystals, 1.35 g (46.8%), m.p. 78–79° C. ¹H NMR (DMSO-d₆): δ 1.08 (s, 6), 1.84 (m, 2), 2.36 (s, 3), 2.61 (m, 2), 7.26 (d, 2), 7.60 (d, 2).

EXAMPLE 39

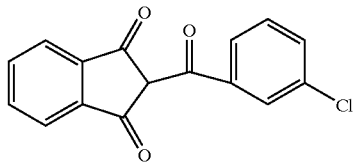

Preparation of 2-(3-Chlorobenzoyl)-1,3-indanedione

A 25-mL 3-neck round bottom flask was charged with 4-nitrophenyl 3-chlorobenzoate (0.64 g, 2.3 mmol), indane-1,3-dione (0.39 g, 2.7mmol) and (methyl sulfoxide)-d₆ (5.0 g). The mixture was heated to 80° C. and potassium fluoride (0.60 g, 10 mmol) was added in a single portion. After stirring at 80° C. for 7 hours, the mixture was cooled, partitioned between diethyl ether-ethyl acetate (1:1, 100 mL) and 1N hydrochloric acid (25 mL). The organic layer was washed with additional portions of 1N hydrochloric acid (3×10 mL), then with brine (10 mL), dried over magnesium sulfate, filtered, and evaporated to leave a brown solid (1.05 g).

This solid was partitioned between diethyl ether (75 mL) and half-saturated aqueous sodium bicarbonate (30 mL). The organic layer was extracted with water (15 mL, 2×10 mL), then brine (10 mL). The aqueous layers were combined, 1N hydrochloric acid (25 mL) was added, and the resulting mixture was extracted with dichloromethane (50 mL, 2×25 mL). The dichloromethane layers were combined, dried over magnesium sulfate, and evaporated to a brown solid residue (0.56 g).

This residue was chromatographed on silica gel (25 g), eluting with dichloromethane. Concentration of fractions containing the product afforded the title compound as a tan solid, 0.17 g (26%), m.p. 148–149° C. (diethyl ether). ¹H NMR (CDCl₃): δ 7.47 (m, 1), 7.60 (m, 1), 7.76 (m, 2), 7.89 (m, 2), 8.08 (m, 1), 8.15 (m, 1). MS (AP-)***: 283, 285 (M-1, 1×Cl).

*** Mass Spectrometry Technique—Atmospheric Pressure Chemical Ionization in the negative.

EXAMPLE 40

Preparation of 2-(3-Chlorobenzoyl)-1,3-indanedione using Acetone Cyanohydrin

A 50-mL round bottom flask was charged with 4-nitrophenyl 3-chlorobenzoate (1.05 g, 3.8 mmol), indane-1,3-dione (0.73 g, 5.0 mmol), and acetonitrile (5 mL). Triethylamine (0.85 g, 8.4 mmol) was added, followed by acetone cyanohydrin (50 μL, 0.55 mmol), and the mixture was heated under reflux for 6 hours. The reaction mixture was then cooled and partitioned between ethyl acetate (200 mL) and 1N hydrochloric acid (50 mL). The organic layer was separated, washed with additional portions of 1N hydrochloric acid (3×20 mL) and brine (20 mL), dried over magnesium sulfate, filtered, and evaporated to a dark residue (2.73 g).

The residue was partitioned between diethyl ether (150 mL) and half-saturated aqueous sodium bicarbonate (60 mL). The organic layer was further extracted with water (30 mL, 2×20 mL), then with brine (20 mL). These aqueous layers were combined, acidified to pH1 with 1N hydrochloric acid (50 mL), and the resulting precipitate was filtered, washed with water, and dried to leave a brown solid (0.92 g).

This solid was chromatographed on silica gel (25 g), eluting with dichloromethane. Concentration of fractions containing the product afforded the title compound as a light brown powder, 0.31 g (29%), identical by ¹H NMR with the product of Example 39, m.p. 147–149° C. (hexanes-diethyl ether).

EXAMPLE 41

Preparation of 2-(3-Chlorobenzoyl)-1,3-indanedione using Potassium Cyanide

The procedure of Example 40 was followed, except that potassium cyanide (33 mg, 0.51 mmol) was used in place of acetone cyanohydrin. The title compound was obtained as a light brown powder, 0.15 g (14%), identical by ¹H NMR with the product of Example 39, m.p. 146–148° C. (hexanes-diethyl ether).

What is claimed is:

1. A method for preparing an acylated cyclic product of Formula 1:

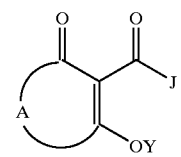

wherein

A is a linking group comprising an optionally substituted backbone segment consisting of 2 to 4 atoms selected from carbon atoms and 0 to 2 nitrogen, 0 to 2 oxygen and 0 to 2 sulfur atoms;

J is an optionally substituted, carbon-linked hydrocarbyl group; and

Y is H or a salt cation;

the process comprising contacting a phenyl ester of Formula 2:

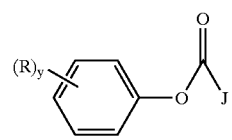

wherein y is 0, 1, 2 or 3; and each R is independently selected from electron-withdrawing groups;

with a cyclic compound of Formula 3:

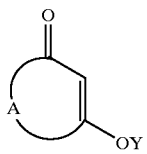

in the presence of a source of cyanide or fluoride ion.

2. The method of claim 1 wherein the source of the cyanide ion is selected from the group consisting of sodium cyanide, potassium cyanide, zinc cyanide, hydrogen cyanide and acetone cyanohydrin.

3. The method of claim 1 wherein the source of fluoride ion is selected from the group consisting of ammonium, phosphonium and alkali metal fluoride salts.

4. The method of claim 3 wherein the source of fluoride ion is selected from the group consisting of potassium fluoride and cesium fluoride.

5. The method of claim 3 wherein the source of fluoride is spray-dried potassium fluoride.

6. The method of claim 1 further comprising adding a source of basicity.

7. The method of claim 6 wherein the source of basicity is an organic amine or an ionic base.

8. The method of claim 6 wherein the source of basicity is selected from the group consisting of lithium carbonate, sodium carbonate and potassium carbonate.

9. The method of claim 6 wherein the source of basicity is a tertiary amine.

10. The method of claim 1 further comprising adding a phase transfer catalyst.

11. The method of claim 1 wherein R is selected from the group consisting of $NO_2$, $COOR^1$, $COR^1$, $SO_2R^1$, $CN$, $CF_3$, $F$, $CON(R^1)_2$ and $SO_2N(R^1)_2$ wherein each $R^1$ is independently selected from $C_1$–$C_6$ alkyl groups.

12. The method of claim 1 wherein J is an optionally substituted alkyl, alkenyl, alkynyl, cycloalkenyl or aryl group.

13. The method of claim 12 wherein J is an aryl group selected from the group consisting of benzene, thiophene, pyridine, pyridazine, pyrazine, pyrimidine, pyrrole, triazine, triazole and furan.

14. The method of claim 1 wherein A together with the 1,3-dione moiety, or an enolic tautomer of the 1,3-dione moiety, forms an optionally substituted 5-, 6- or 7-membered carbocyclic or heterocyclic, saturated, partially unsaturated or heterocyclic ring, optionally fused with another optionally substituted carbocyclic or heterocyclic, saturated, partially unsaturated or aromatic, monocyclic or polycyclic ring system to form a polycyclic ring system.

15. The method of claim 14 wherein the optional substituents on A are independently selected from the group consisting of alkyl, alkenyl, alkynyl, cycloalkyl, cycloalkenyl, cycloalkyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, aryloxy, alkylthio, alkenylthio, alkynylthio, alkylsulfinyl, alkenylsulfinyl, alkynylsulfinyl, arylsulfinyl, alkylsulfonyl, alkenylsulfonyl, alkynylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyloxy, alkenylaminocarbonyloxy, alkynylaminocarbonyloxy, arylaminocarbonyloxy, alkoxycarbonylamino, alkenyloxycarbonylamino, alkynyloxycarbonylamino and aryloxycarbonylamino, each further optionally substituted, and halogen, cyano and nitro.

* * * * *